(12) United States Patent
Zhang et al.

(10) Patent No.: US 11,872,196 B2
(45) Date of Patent: *Jan. 16, 2024

(54) USE OF CANNABIDIOL IN TREATMENT OF PULMONARY HYPERTENSION

(71) Applicant: DEYI PHARMARMACEUTICAL LTD., Kunming (CN)

(72) Inventors: Ke Zhang, Beijing (CN); Xin Tan, Beijing (CN); Zhaohui Yu, Beijing (CN); Xiangdong Li, Beijing (CN)

(73) Assignee: DEYI PHARMARMACEUTICAL LTD., Kunming (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,162

(22) Filed: Mar. 22, 2023

(65) Prior Publication Data

US 2023/0404941 A1    Dec. 21, 2023

Related U.S. Application Data

(63) Continuation of application No. 16/630,428, filed as application No. PCT/CN2017/093367 on Jul. 18, 2017, now Pat. No. 11,666,542.

(51) Int. Cl.
| | | |
|---|---|---|
| *A61K 31/05* | (2006.01) | |
| *A61P 9/12* | (2006.01) | |
| *A61P 11/00* | (2006.01) | |
| *A61K 31/191* | (2006.01) | |
| *A61K 31/192* | (2006.01) | |
| *A61K 31/4985* | (2006.01) | |
| *A61K 31/506* | (2006.01) | |
| *A61K 31/519* | (2006.01) | |
| *A61K 31/53* | (2006.01) | |
| *A61K 36/185* | (2006.01) | |
| *A61K 45/06* | (2006.01) | |

(52) U.S. Cl.
CPC ............ *A61K 31/05* (2013.01); *A61K 31/191* (2013.01); *A61K 31/192* (2013.01); *A61K 31/4985* (2013.01); *A61K 31/506* (2013.01); *A61K 31/519* (2013.01); *A61K 31/53* (2013.01); *A61K 36/185* (2013.01); *A61K 45/06* (2013.01); *A61P 9/12* (2018.01); *A61P 11/00* (2018.01)

(58) Field of Classification Search
None
See application file for complete search history.

(56) References Cited

U.S. PATENT DOCUMENTS

| | | | |
|---|---|---|---|
| 10,105,343 | B2 | 10/2018 | Kubby |
| 2004/0049059 | A1 | 3/2004 | Mueller |

OTHER PUBLICATIONS

Atakan, "Cannabis, a complex plant: different compounds and different effects on individuals", Ther. Adv. Psychopharmacol. Dec. 2012; 2(6): 241-254.

Diagnosis and Treatment of Pulmonary Hypertension, Trenton D. Nau Ser, M.D., and Steven W. Stites, M.D., University of Kansas Medical Center, Kansas City, Kansas Am Fam Physician. May 1, 2001 ;63(9): 1789-1799.

*Primary Examiner* — Michael V Meller
(74) *Attorney, Agent, or Firm* — Platinum Intellectual Property PC (57) ABSTRACT

The present invention belongs to the field of medicine, and relates to use of cannabidiol (CBD) in the treatment of pulmonary arterial hypertension. The CBD can be used as the only active ingredient or combined with other active ingredients to prepare a medicament for treating pulmonary arterial hypertension. Specifically, the present invention relates to use of any one selected from (1) to (3) in the preparation of a medicament for treating and/or preventing pulmonary arterial hypertension: (1) CBD, (2) a plant extract containing the CBD; and preferably, the plant extract is a *cannabis* extract, and (3) a pharmaceutical composition containing the CBD and one or more pharmaceutically acceptable adjuvants. In the present invention, upon experimental researches, it has found that the CBD has the function of inhibiting pulmonary arterial hypertension, and is especially suitable for treating the pulmonary arterial hypertension caused by hypoxemia.

3 Claims, 4 Drawing Sheets

Specification includes a Sequence Listing.

SEQUENCE LISTING

```
Sequence total quantity: 6
SEQ ID NO: 1            moltype = DNA  length = 23
FEATURE                 Location/Qualifiers
misc_feature            1..23
                        note = Primer
source                  1..23
                        mol_type = other DNA
                        organism = synthetic construct
SEQUENCE: 1
ccctcacact cagatcatct tct                                          23

SEQ ID NO: 2            moltype = DNA  length = 19
FEATURE                 Location/Qualifiers
misc_feature            1..19
                        note = Primer
source                  1..19
                        mol_type = other DNA
                        organism = synthetic construct
SEQUENCE: 2
gctacgacgt gggctacag                                               19

SEQ ID NO: 3            moltype = DNA  length = 23
FEATURE                 Location/Qualifiers
misc_feature            1..23
                        note = Primer
source                  1..23
                        mol_type = other DNA
                        organism = synthetic construct
```

-continued

```
SEQUENCE: 3
gaggatacca ctcccaacag acc                                                23

SEQ ID NO: 4           moltype = DNA  length = 21
FEATURE                Location/Qualifiers
misc_feature           1..21
                       note = Primer
source                 1..21
                       mol_type = other DNA
                       organism = synthetic construct
SEQUENCE: 4
aagtgcatcg ttgttcatac a                                                  21

SEQ ID NO: 5           moltype =   length =
SEQUENCE: 5
000

SEQ ID NO: 6           moltype = DNA  length = 24
FEATURE                Location/Qualifiers
misc_feature           1..24
                       note = Primer
source                 1..24
                       mol_type = other DNA
                       organism = synthetic construct
SEQUENCE: 6
agttgaccac caccaggtga gaat                                               24
```

USE OF CANNABIDIOL IN TREATMENT OF PULMONARY HYPERTENSION

RELATED APPLICATIONS

This application is a continuation application of U.S. application Ser. No. 16/630,428 filed Jan. 10, 2020, which is a United States National Stage Application filed under 35 U.S.C 371 of PCT Patent Application Serial No. PCT/CN2017/093367, filed Jul. 18, 2017, the disclosure of all of which are hereby incorporated by reference in their entirety.

INCORPORATION BY REFERENCE

Under 37 CFR 1.823, this application incorporates the Sequence Listing that is jointly filed (file title: 7_6106_0007_SequenceListing; file size: 2 KB) into the present disclosure.

FIELD

The present invention belongs to the field of medicine, and relates to use of cannabidiol in the treatment of pulmonary arterial hypertension.

BACKGROUND

Pulmonary arterial hypertension (PAH) has a complex etiology and is caused by a variety of heart, lung, or pulmonary vascular diseases. The PAH is pathologically characterized by pulmonary arteriolar vascular remodeling and pulmonary arterial vascular smooth muscle proliferation, is manifested as increased pulmonary circulation pressure and resistance, may result in an increased right cardiac load, right cardiac insufficiency and decreased pulmonary blood flow, and thus causes a series of clinical manifestations; and the PAH usually develops progressively in the course of disease. In particular, right heart failure caused by the increased pulmonary artery vascular tone is a serious threat to human life and health.

The PAH is divided into two categories: primary and secondary. With the gradual deepening of understanding of the PAH, the World Health Organization (WHO) classified PAH according to its etiology, pathophysiology, therapeutic regimen and prognosis in "PAH Conference" in 2003, and the American College of Chest Physicians (ACCP) and the European Society of Cardiovascular Diseases (ESC) revised this in 2004. This classification method has guiding significance for the treatment of PAH patients. It is generally believed that it is the PAH when the mean pulmonary artery pressure detected by a right cardiac catheter is ≥25 mmHg in a calm state (Badesch et al., 2009). The PAH can be graded according to the resting PAPm, with a mild level of 26-35 mm Hg; a moderate level of 36-45 mmHg; and a severe level of greater than 45 mmHg.

The PAH mainly involves the pulmonary arteries and the right heart, and is manifested by right ventricular hypertrophy and right atrial dilatation. The main pulmonary artery is dilated and the surrounding pulmonary arterioles are sparse. Pulmonary arteriolar endothelial cells and smooth muscle cells are proliferated and hypertrophied, the intima fibrosis is thickened, tunica media are hypertrophied, and the lumen is narrow, occlusive, twisted and deformed and changes in clusters. Pulmonary venules can also have intimal fibrosis hyperplasia and lumen obstruction. Other manifestations of the PAH patient also include hypertrophy of pulmonary artery adventitias and veins, increased expression of TGF-β, and increased expression of matrix proteins such as elastin, fibronectin, cytochrome C and mucopolysaccharide.

The PAH is a disease that can be treated, but there is no effective method for curing the PAH at present. Traditional treatment methods include oxygen inhalation, cardiotonic, diuresis, calcium channel blockers and anticoagulant adjuvant therapeutic agents, which are mainly used for relieving symptoms.

In recent years, the development and popularized use of targeted therapeutic drugs (mainly including prostacyclin drugs, endothelin receptor antagonists, phosphodiesterase-5 inhibitors and newly explored soluble guanylate cyclase agonists, 5-hydroxytryptamine transporter inhibitors, growth factor inhibitors, Rho kinase inhibitors, etc.), and therapeutic methods such as living lung transplantation, and the like have greatly improved the prognosis of the patient.

Although these drugs can relieve the symptoms of PAH to a certain extent, the PAH is still an incurable disease with high mortality. The median survival time of a patient that receives treatment is only 2.7 years. Currently, there is still no specific cure method for the PAH. Therefore, it is particularly urgent to find a new specific therapeutic drug.

SUMMARY

After in-depth research and creative work, the inventor has surprisingly found that cannabidiol can effectively inhibit pulmonary arterial hypertension (PAH) and is especially suitable for treating the PAH caused by hypoxemia. Thus, the following invention is provided:

An aspect of the present invention relates to use of any one selected from (1) to (3) in preparation of a medicament for treating and/or preventing pulmonary arterial hypertension (PAH):

(1) cannabidiol, or a pharmaceutically acceptable salt or ester thereof, (2) a plant extract containing cannabidiol; and preferably, the plant extract is a *cannabis* extract such as an industrial *cannabis* extract, and (3) a pharmaceutical composition containing the cannabidiol or the pharmaceutically acceptable salt or ester thereof, and one or more pharmaceutically acceptable adjuvants.

For the use in one embodiment of the present invention, the PAH is primary or secondary PAH; and preferably is arterial PAH (such as idiopathic PAH, heritable PAH, PAH caused by drugs and poisons or persistent PAH of the newborn), PAH related to left heart diseases (such as PAH caused by cardiac systolic dysfunction, PAH caused by diastolic dysfunction, or PAH caused by valvular diseases), PAH caused by pulmonary diseases (such as PAH caused by chronic obstructive pulmonary diseases, PAH caused by emphysema or PAH caused by pulmonary interstitial diseases), PAH caused by hypoxemia (such as PAH caused by sleep apnea syndromes, or PAH caused by chronic altitude diseases such as altitude heart diseases), or chronic thromboembolic PAH; and more preferably is PAH caused by hypoxemia.

Cannabidiol (CBD) is one of cannabinoid substances, and its structural formula is as shown in the following formula I:

Formula I

The CBD, i.e., the compound of the formula I, can be purchased commercially (e.g., purchased from Sigma, etc.) or synthesized through the available technology by using commercially available raw materials. The synthesized CBD can be further purified by column chromatography, liquid-liquid extraction, molecular distillation or crystallization. In addition, the CBD can also be extracted from *cannabis*, especially industrial *cannabis*.

In the present invention, upon experimental researches, it is found that, the cannabidiol and the aforementioned compound of the present invention have obvious therapeutic effects on animal models with PAH caused by hypoxia and drug induction.

The pharmaceutically acceptable salt of the cannabidiol includes, but not limited to, organic ammonium salts, alkali metal salts (sodium salts, and potassium salts), alkaline earth metal salts (magnesium salts, strontium salts, and calcium salts), etc.

In some embodiments of the present invention, the pharmaceutically acceptable salt of the cannabidiol may be a salt formed from the cannabidiol (CBD) with sodium hydroxide, potassium hydroxide, calcium hydroxide, magnesium hydroxide, aluminum hydroxide, lithium hydroxide, zinc hydroxide, barium hydroxide, ammonia, methylamine, dimethylamine, diethylamine, methylpyridine, ethanolamine, diethanolamine, triethanolamine, ethylenediamine, lysine, arginine, ornithine, choline, N,N'-diphenylmethylethylenediamine, chloroprocaine, diethanolamine, procaine, N-benzyl phenylethylamine, N-methylglucosamine piperazine, tris(hydroxymethyl)-aminomethane, etc.

In some embodiments of the present invention, the pharmaceutically acceptable ester of the cannabidiol may be a monoester of the cannabidiol and a $C_0$-$C_6$ alkyl carboxylic acid, or may be a diester of the cannabidiol and two identical or different $C_0$-$C_6$ alkyl carboxylic acids, the $C_0$-$C_6$ alkyl carboxylic acid may be a linear alkyl carboxylic acid, a branched alkyl carboxylic acid or a cycloalkyl carboxylic acid, such as, HCOOH, $CH_3COOH$, $CH_3CH_2COOH$, $CH_3(CH_2)_2COOH$, $CH_3(CH_2)_3COOH$, $CH_3(CH_2)_4COOH$, $(CH_3)_2CHCOOH$, $(CH_3)_3CCOOH$, $(CH_3)_2CHCH_2COOH$, $(CH_3)_2CH(CH_2)_2COOH$, $(CH_3)_2CH(CH_3)CHCOOH$, $(CH_3)_3CCH_2COOH$, $CH_3CH_2(CH_3)_2CCOOH$, cyclopropane carboxylic acid, cyclobutane carboxylic acid, and cyclopentane carboxylic acid.

The *cannabis* extract can be a *cannabis*, especially industrial *cannabis*, extract containing cannabidiol, such as an ethanol extracting solution, an ethanol extractum, etc. wherein the content of the cannabidiol is not particularly limited, and the content of the cannabidiol in the *cannabis* extract can be further increased by means known to those skilled in the art, such as concentration, etc. In one embodiment of the present invention, the *cannabis* extract is an extractum, and preferably the cannabidiol content is 18%-25%.

Another aspect of the present invention relates to use of any one selected from (1) to (3) in the preparation of a medicament for inhibiting inflammation, a medicament for inhibiting expression of inflammatory factors, or a medicament for promoting expression of a gene for inhibiting inflammation (e.g., a $MgI_2$ gene):

(1) cannabidiol, or a pharmaceutically acceptable salt or ester thereof,
(2) a plant extract containing cannabidiol; and preferably, the plant extract is a *cannabis* extract, and
(3) a pharmaceutical composition containing the cannabidiol or the pharmaceutically acceptable salt or ester thereof, and one or more pharmaceutically acceptable adjuvants.

For the use in one embodiment of the present invention, the inflammation is chronic low-grade inflammation.

For the use in one embodiment of the present invention, the inflammatory factor is selected from TNF-α and IL-6, and especially human TNF-α and human IL-6.

Another aspect of the present invention relates to a pharmaceutical composition, including cannabidiol or a pharmaceutically acceptable salt or ester thereof, or including a plant extract (e.g., a *cannabis* extract) containing cannabidiol or a pharmaceutically acceptable salt or the cannabidiol is only active ingredient of the pharmaceutical composition ester thereof, and one or more pharmaceutically acceptable adjuvants.

In one embodiment of the present invention, cannabidiol is the only active ingredient of the pharmaceutical composition. In another embodiment of the present invention, cannabidiol is used in combination with one or more other active ingredients known for preventing and treating pulmonary arterial hypertension (PAH).

For the pharmaceutical composition in one embodiment of the present invention, the pharmaceutical composition further includes any one or more selected from prostacyclin drugs, endothelin receptor antagonists, phosphodiesterase-5 inhibitors, soluble guanylate cyclase agonists, 5-hydroxytryptamine transporter inhibitors, growth factor inhibitors, and Rho kinase inhibitors.

For the pharmaceutical composition in one embodiment of the present invention, wherein,
the prostacyclin drugs are selected from any one or more of Benapnost, Treprostinil, iloprost and Ventavis;
the endothelin receptor antagonist is bosentan; and/or
the phosphodiesterase-5 inhibitor is selected from Sildenafil, Vardenafil and Tadalafil.

The preparation form of the pharmaceutical composition can be any pharmaceutical dosage form, and the dosage forms include tablets, sugar-coated tablets, film-coated tablets, enteric-coated tablets, capsules, hard capsules, soft capsules, oral liquids, buccal agents, granules, dissolved medicines, pills, pulvis, pastes, sublimed preparations, suspensions, powders, solutions, injections, suppositories, ointments, plasters, creams, sprays, drops and patches; and preferably oral dosage forms, such as capsules, tablets, oral liquids, granules, pills, pulvis, sublimed preparations, pastes, etc. The oral dosage form may contain common excipients, such as a binder, a filler, a diluent, a tableting agent, a lubricant, a disintegrant, a colorant, a flavoring agent and a humectant, and the tablets may be coated if necessary. Suitable fillers include cellulose, mannitol, lactose and other similar fillers; suitable disintegrants include starch, polyvinylpyrrolidone, and starch derivatives such as sodium starch glycolate; and suitable lubricants include, for example, magnesium stearate. Suitable pharmaceutically acceptable humectants include sodium dodecyl sulfate.

Preferably, the pharmaceutical composition is an oral preparation. Upon tests the inventor has found that, the medicament prepared from the cannabidiol has an obvious therapeutic effect on a mouse suffering from PAH through oral gavage.

The treatment and/or prevention effective dosage of the pharmaceutical composition of the present invention is 0.1-200 mg/kg body weight/day. The effective dosage of the pharmaceutical composition of the present invention is preferably 0.1-100 mg/kg body weight/day; and more preferably 0.1-50 mg/kg body weight/day. It is recommended that the effective dosage of the pharmaceutical composition in the human body is preferably 0.1-50 mg/kg body weight/day; and more preferably 0.5-30 mg/kg body weight/day. The "effective dosage for treatment and/or prevention" can be used for single drug administration or combined drug administration for related diseases.

The preferred use method of the pharmaceutical composition (medicament) for treating pulmonary arterial hypertension is oral administration, and the preferred dosage is 0.5-30 mg/kg daily.

Another aspect of the present invention relates to a combined product, including a product 1 and a product 2, wherein:

the product 1 is any one selected from (1) to (3):
(1) cannabidiol, or a pharmaceutically acceptable salt or ester thereof,
(2) a plant extract containing cannabidiol; and preferably, the plant extract is a *cannabis* extract, and
(3) a pharmaceutical composition containing the cannabidiol or the pharmaceutically acceptable salt or ester thereof, and one or more pharmaceutically acceptable adjuvants;

the product 2 is any one or more selected from prostacyclin drugs, endothelin receptor antagonists, phosphodiesterase-5 inhibitors, soluble guanylate cyclase agonists, 5-hydroxytryptamine transporter inhibitors, growth factor inhibitors and Rho kinase inhibitors;
and the products 1 and 2 are each individually packaged; preferably, both products 1 and 2 are in the form of oral preparations.

For the combined product in one embodiment of the present invention, wherein
the prostacyclin drugs are any one or more selected from Benapnost, Treprostinil, iloprost and Ventavis;
the endothelin receptor antagonist is bosentan; and/or
the phosphodiesterase-5 inhibitor is selected from Sildenafil, Vardenafil and Tadalafil.

A further aspect of the present invention relates to a product selected from any one of (1) to (3), used for treating and/or preventing pulmonary arterial hypertension (PAH):
(1) cannabidiol, or a pharmaceutically acceptable salt or ester thereof,
(2) a plant extract containing cannabidiol; and preferably, the plant extract is a *cannabis* extract, and
(3) a pharmaceutical composition containing the cannabidiol or the pharmaceutically acceptable salt or ester thereof, and one or more pharmaceutically acceptable adjuvants.

For the product in one embodiment of the present invention, the PAH is primary or secondary PAH; and preferably is arterial PAH (such as idiopathic PAH, heritable PAH, PAH caused by drugs and poisons or persistent PAH of the newborn), PAH related to left heart diseases (such as PAH caused by cardiac systolic dysfunction, PAH caused by diastolic dysfunction, or PAH caused by valvular diseases), PAH caused by pulmonary diseases (such as PAH caused by chronic obstructive pulmonary diseases, PAH caused by emphysema or PAH caused by pulmonary interstitial diseases), PAH caused by hypoxemia (such as PAH caused by sleep apnea syndromes, or PAH caused by chronic altitude diseases such as altitude heart diseases), or chronic thromboembolic PAH; and more preferably is PAH caused by hypoxemia.

A further aspect of the present invention relates to a product selected from any one of (1) to (3), used for inhibiting inflammation, inhibiting expression of inflammatory factors, or promoting expression of a gene for inhibiting inflammation (e.g., a $MgI_2$ gene):
(1) cannabidiol, or a pharmaceutically acceptable salt or ester thereof,
(2) a plant extract containing cannabidiol; and preferably, the plant extract is a *cannabis* extract, and
(3) a pharmaceutical composition containing the cannabidiol or the pharmaceutically acceptable salt or ester thereof, and one or more pharmaceutically acceptable adjuvants.

For the product in one embodiment of the present invention, the inflammatory factor is selected from TNF-α and IL-6, and especially human TNF-α and human IL-6.

Another aspect of the present invention relates to a method of treating and/or preventing pulmonary arterial hypertension, including the step of administering an effective amount of a product selected from any one of (1) to (3) to a subject in need:
(1) cannabidiol, or a pharmaceutically acceptable salt or ester thereof,
(2) a plant extract containing cannabidiol; and preferably, the plant extract is a *cannabis* extract, and
(3) a pharmaceutical composition containing the cannabidiol or the pharmaceutically acceptable salt or ester thereof, and one or more pharmaceutically acceptable adjuvants.

For the method in one embodiment of the present invention, the subject is a mammal, and especially human beings.

For the method in one embodiment of the present invention, the PAH is primary or secondary PAH; and preferably is arterial PAH (such as idiopathic PAH, heritable PAH, PAH caused by drugs and poisons or persistent PAH of the newborn), PAH related to left heart diseases (such as PAH caused by cardiac systolic dysfunction, PAH caused by diastolic dysfunction, or PAH caused by valvular diseases), PAH caused by pulmonary diseases (such as PAH caused by chronic obstructive pulmonary diseases, PAH caused by emphysema or PAH caused by pulmonary interstitial diseases), PAH caused by hypoxemia (such as PAH caused by sleep apnea syndromes, or PAH caused by chronic altitude diseases such as altitude heart diseases), or chronic thromboembolic PAH; and more preferably is PAH caused by hypoxemia.

A further aspect of the present invention relates to a method of inhibiting inflammation, inhibiting expression of inflammatory factors or promoting expression of a gene for inhibiting inflammation (e.g., a $MgI_2$ gene), including the step of administering an effective amount of a product selected from any one of (1) to (3) to a subject in need:
(1) cannabidiol, or a pharmaceutically acceptable salt or ester thereof,
(2) a plant extract containing cannabidiol; and preferably, the plant extract is a *cannabis* extract, and
(3) a pharmaceutical composition containing the cannabidiol or the pharmaceutically acceptable salt or ester thereof, and one or more pharmaceutically acceptable adjuvants.

For the method in one embodiment of the present invention, the inflammation is chronic low-grade inflammation.

For the method in one embodiment of the present invention, the inflammatory factor is selected from TNF-α and IL-6.

It should be pointed out that, the dosage and use method of the active ingredient cannabidiol depend on many factors, including the age, body weight, gender, natural health status, and nutritional status of the patient, the activity intensity of the compound, the administration time, the metabolic rate, the severity of the disease and the subjective judgment of the physician. The dosage (effective amount) of the used cannabidiol is preferably 0.1-50 mg/kg body weight/day, more preferably 0.5 mg/kg-30 mg/kg body weight/day, 0.5 mg/kg-20 mg/kg body weight/day, 5 mg/kg-30 mg/kg body weight/day or 5 mg/kg-20 mg/kg body weight/day, further more preferably 0.5 mg/kg-10 mg/kg body weight/day, and particularly preferably 0.5 mg/kg-5 mg/kg body weight/day. Preferably, the administering is performed orally.

In the present invention, the term "effective amount" refers to a dose that can achieve the treatment, prevention, alleviation and/or remission of the disease or condition of the present invention in a subject.

The term "subject" may refer to a patient or other animals, especially mammals, such as human, a dog, a monkey, a cow, a horse, etc., that receives/receive the composition of the present invention to treat, prevent, alleviate, and/or relieve the disease or condition of the present invention.

The term "disease and/or condition" refers to a physical state of the subject, which is related to the disease and/or condition of the present invention.

In the present invention, the term "pulmonary arterial hypertension" and the commonly referred hypertension are two distinctly different diseases. A heart of human is divided into a left heart system and a right heart system. What we usually call hypertension refers to the pressure rise in arteries started from the left heart system for supplying blood to the whole body; and the arteries started from the right heart system are specially responsible for supplying blood to the lung, and are called pulmonary arteries, and the pressure rise in such arteries is called pulmonary arterial hypertension.

Pulmonary arterial hypertension (PAH) is a disease or pathophysiological syndrome caused by abnormal pressure rise in pulmonary artery due to known or unknown reasons. The pulmonary circulation disorder and right heart overload exist, leading to failure and even death of the right heart, and in the later stage of PAH patients, hypotension may develop hypotension due to cardiac ejection dysfunction.

The term "hypertension" refers to a clinical syndrome mainly characterized by an increase in systemic arterial blood pressure (systolic and/or diastolic pressure) (the systolic pressure ≥140 mm Hg, and the diastolic pressure ≥90 mm Hg), which may be accompanied by functional or organic damage to organs such as the heart, brain and kidney.

The term "TNF-α" refers to the tumor necrosis factor-α, which is a cytokine involved in systemic inflammation, meanwhile is also one of many cytokines that cause acute phase reactions, and is mainly secreted by macrophages. The main function of the tumor necrosis factor α is to regulate the function of immune cells. In the present invention, unless otherwise specified, TNF-α refers to a protein as shown by the GenBank accession number: NP_038721.1, or a fragment thereof having the function of the TNF-α. In one embodiment of the present invention, the nucleic acid sequence of the TNF-α gene is as shown in Gene ID: 21926 or its degenerate sequence.

The term "IL-6" refers to interleukin 6, which is a cytokine and belongs to aone of interleukins. IL-6 can be produced by fibroblasts, monocytes/macrophages, T lymphocytes, B lymphocytes, epithelial cells, keratinocytes or various tumor cells. Interleukin 6 can stimulate the proliferation, and differentiation of cells involved in immune response, and improve the function of the cells. In the present invention, unless otherwise specified, IL-6 refers to a protein as shown by the GenBank accession number: NP_001300983.1, or a fragment thereof having the function of IL-6. In one embodiment of the present invention, the nucleic acid sequence of the IL-6 gene is as shown in Gene ID: 16193 or its degenerate sequence.

The term "$MgI_2$" refers to macrophage galactose N-acetyl-galactosamine specific lectin 2. In the present invention, unless otherwise specified, $MgI_2$ refers to a protein as shown by the GenBank accession number: NP_660119.1, or a fragment thereof having the function of $MgI_2$. In one embodiment of the present invention, the nucleic acid sequence of the $MgI_2$ gene is as shown in Gene ID: 216864 or its degenerate sequence.

In the present invention, unless otherwise specified, the products 1 and 2 are only for clear reference, and do not have the meaning of order.

In the present invention, unless otherwise specified, the *cannabis* is preferably industrial *cannabis*; and the *cannabis* extract is preferably an industrial *cannabis* extract.

Beneficial Effects of the Invention

In the invention, upon experimental researches, the effect of cannabidiol on inhibiting pulmonary arterial hypertension has been found, showing that cannabidiol has a good therapeutic effect on pulmonary arterial hypertension, and is especially suitable for treating pulmonary arterial hypertension caused by hypoxemia.

DETAILED DESCRIPTION OF THE EMBODIMENTS

Hereinafter, embodiments of the present invention will be described in detail with reference to examples, but those skilled in the art will understand that the following examples are only for illustrating the present invention and should not be considered as limiting the scope of the present invention. If no specific conditions are specified in the examples, the embodiments will be carried out according to conventional conditions or the conditions recommended by the manufacturer. All of the used agents or instruments which are not specified with the manufacturer are conventional commercially-available products.

Example 1: Test on Effect of Cannabidiol on Pulmonary Arterial Hypertension Caused by Hypoxia 1. Experimental Animals, Reagents and Instruments (1) Experimental Animals Healthy and lively C57BL/6 mice at the age of 4-6 weeks, with glossy hair colors, and body weights of (25.15±2.15) g (Laboratory Animal Center of Academy of Military Medical Sciences, SPF grade). The mice were divided into four groups:

Group 1 (wild-type normoxia, used as a control group): 10 female mice and 10 male mice under normoxia conditions;

Group 2 (wild-type hypoxia, used as a control group): 10 female mice and 10 male mice under hypoxia conditions;

Group 3 (10 mg/kg, used as an experimental group): 10 female mice and 10 male mice were treated with 10 mg/kg by gavage under hypoxia conditions;

Group 4 (50 mg/kg, used as an experimental group): 10 female mice and 10 male mice were treated with 50 mg/kg by gavage under hypoxia conditions.

(2) Administration Method

The mice of groups 2-4 were placed in an animal feeding chamber under normal pressure and hypoxia, the oxygen concentration in the chamber was maintained at 9%-11%, and the temperature in the chamber was maintained at 22-26° C. The mice of group 1 inhaled normal atmosphere air, and the other conditions were the same as those for mice of groups 2-4.

Previous research results showed that a pulmonary arterial hypertension model using the significant increase in right ventricular systolic pressure as a standard could be established after 14 days of continuous hypoxia in mice (Ricard, N., Tu, L., Le Hiress, M., Huertas, A., Phan, C., Thuillet, R., Sattler, C., Fadel, E., Seferian, A., Montani, D., et al. (2014). Increased pericyte coverage mediated by endothelial-derived fibroblast growth factor-2 and interleukin-6 is a source of smooth muscle-like cells in pulmonary hypertension. Circulation 129, 1586-1597). In order to explore whether CBD has a therapeutic effect on pulmonary arterial hypertension or not, the inventor first treated mice for 14 days in a continuous hypoxia environment to establish a model of pulmonary arterial hypertension (the groups 2-4), and then administration was started from day 15 to day 21 through gavage once a day, the mice were treated every day for 7 days (the group 3-4), and detection was performed on day 21.

The specific detection steps were described in Part 2 "Experimental Method" hereafter.

(3) Experimental Reagents

Sodium pentobarbital (sigma); cannabidiol (Yunnan Hansu Biotechnology Co.,Ltd); Crystal Violet, Victoria Blue B (Sinopharm Chemical Reagent Co., Ltd.); New fuchsine (Tokyo Chemical Industry).

(4) Experimental Instruments

A multi-channel physiological recorder (BE-EH4) from B&E TEKSYSTEMS LTD; an OLYMPUS microscope (CX4) from Olympus (China) Co., Ltd. (OCN); a hypoxia box (CJ-DO2) from Changsha Changjin Technology Co., Ltd; a fluorescence quantitative PCR instrument (Light Cycler480II) from Roche Applied Science.

2. Experimental Method (1) Determination of Right Ventricular Systolic Pressure (RVSP)

On day 21, the mice were anesthetized by intraperitoneal injection of sodium pentobarbital (35 mg/kg), and the right ventricular systolic pressure was measured by using a catheter matched with a physiological instrument with reference to the right-heart catheterization reported by Song et al. (Song, Y., Jones, J. E., Beppu, H., Keaney, J. F., Jr., Loscalzo, J., and Zhang, Y. Y. (2005). Increased susceptibility to pulmonary hypertension in heterozygous BMPR2-mutant mice. Circulation 112, 553-562). A tip of the catheter was connected with a signal acquisition and processing system of the multi-channel physiological recorder, and the position of the tip of the catheter was judged according to the blood pressure values and the migration changes of waveforms of the pressure curve displayed by a monitor. After the catheter entered the right ventricle, RVSP was determined and recorded.

(2) Measurement of Right Ventricular Hypertrophy (RVH)Index

According to the method by Ryan et al., after anesthesia of a mouse, the thoracic cavity of the mouse was opened to pick the heart, all blood vessels and ventricles were stripped off from the heart, the right ventricle was cut off, the weight of the right ventricle and the weights of the left ventricle plus diaphragm were weighed respectively, and the weight of the right ventricle was divided by the combined weight of the left ventricle and diaphragm (RV/(LV+S)).

(3) HE Staining

Sample: paraffin sections of mouse lung tissue.

Objective: observing the pathology of lung tissues to detect whether there is a vascular wall thickening phenomenon or not.

The cut paraffin sections were placed into an oven at 55° C. for 10 min.

1) the paraffin sections were dewaxed and went downward to 70% ethanol;
  xylene I: 15 min
  xylene II: 7 min
  1:1 toluene-ethanol solution: 5 min
  Ethanol of various stages: each for 5 min
2) staining with a hematoxylin solution for 10-15 min;
3) rinsing with tap water for 2 min;
4) differentiation in a 0.5% hydrochloric acid-alcohol solution for 8 s;
5) turning back to blue with tap water for 10 min;
6) 70% alcohol →80% alcohol, each for 2 min;
7) 0.5% eosin-alcohol dye liquor for 50-70 s;
8) color separation with 90% ethanol and 95% ethanol, each for 3 min;
9) dehydrating with absolute ethanol I and II, each for 3 min;
10) absolute ethanol:xylene (1:1) for 3 min;
11) xylene I for 3 min;
12) xylene II for 3 min;
Mounting with a neutral gum;

After the completion of staining, the nucleus was presented as blue-purple, and the cytoplasm was presented as pink.

(4) Elastic Fiber Staining (Elastic Staining)

Sample: paraffin sections of mouse lung tissue.

Preparation of dye liquor: 1 g of Victorian Blue B.

1 g of New Fuchsin, and 1 g of Crystal Violet.

The materials were dissolved in 200 ml of hot water, 4 g of resorcinol, 4 g of dextrin and 50 ml of 30% ferric chloride (prepared immediately before use) were sequentially added, the mixture was boiled for 5 min and filtered, the precipitate and the filter paper were dissolved in 200 ml of 95% ethanol, boiled for 15 min-20 min and filtered (in a water bath), and supplemented with 95% ethanol to 200 ml, and finally 2 ml of concentrated hydrochloric acid was added. The dye liquor was sealed and stored in dark place.

Staining Method xylene I: 10 min; xylene II: 10 min; 100% ethanol: 5 min; 90% ethanol: 5 min; tap water: 5 min; 0.5% potassium permanganate for 5 min; rinsing with tap water for 2-3 min; a 1% oxalic acid solution for 2-3 min (just for bleaching); rinsing with tap water for 2-3 min; 95% ethanol for 2-3 min; staining with an Elastic dye liquor for 2 h; washing the dye liquor away with 95% ethanol; rinsing with tap water for 2-3 min; staining with a Van Gieson dye liquor for 1 min; dehydrating rapidly: 80% ethanol for 1 min, 90% ethanol for 1 min, absolute ethanol I for 5 min, absolute ethanol II for 5 min, xylene I for 5 min, and xylene II for 5 min.

(5) Vascular Remodeling Rate

The method by Keegan et al. (Keegan, A., Morecroft, I., Smillie, D., Hicks, M. N., and MacLean, M. R. (2001). Contribution of the 5-HT(1B) receptor to hypoxia-induced pulmonary hypertension: converging evidence using 5-HT (1B)-receptor knockout mice and the 5-HT(1B/1D)-receptor antagonist GR127935. Circulation research 89, 1231-1239) was employed, wherein counting was conducted with lung paraffin sections that had previously stained for elastic fibers, and 50-100 μm of pulmonary arterioles far away from the central airway were selected for counting, and a blood vessel that had a remodeling part exceeding ½ or more of the circumference of the blood vessel was recorded as a remodeled blood vessel.

(6) Statistical Treatment

The measurement data were expressed as mean±standard error, and statistical processing was conducted by employing SPSS 22.0. The statistical tests were all based on a double-tailed T test.

3. Experimental Results (1) Right Ventricular Systolic Pressure in PAH Mice

Figure 1:
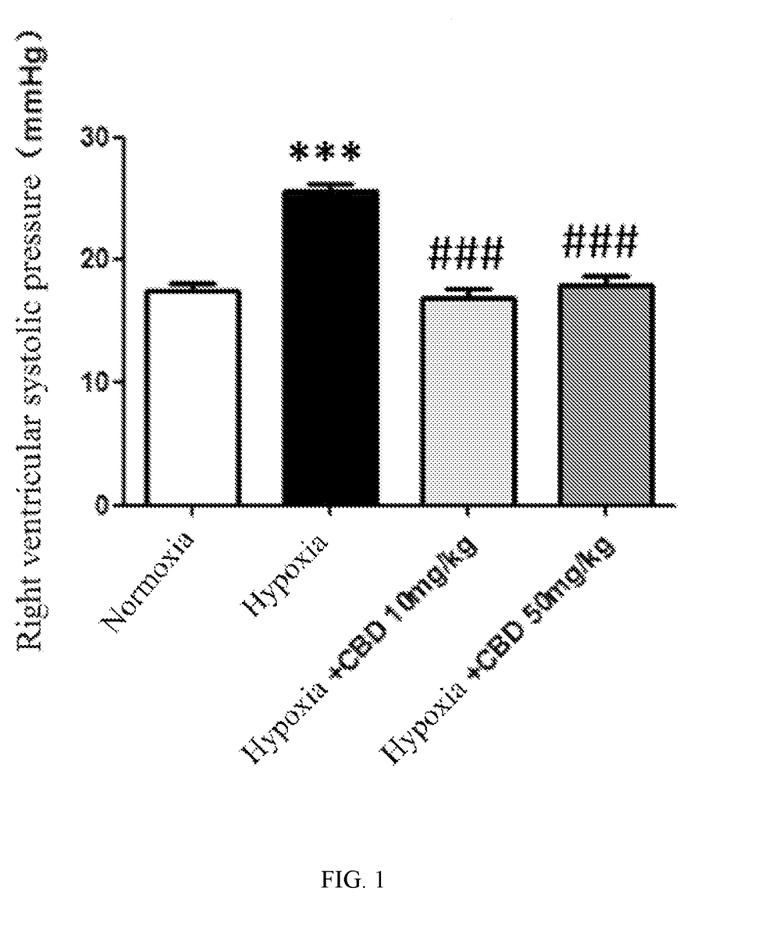
FIG. 1: CBD reduces the increased right ventricular systolic pressure as caused by hypoxia, N=10/group, the numeral value is the average value±standard error, and when the wild-type normoxia group is taken as a reference, ***$P<0.001$; and when the wild-type hypoxia group is taken as a reference, ####$P<0.001$.

The results were as shown in FIG. 1.

After 21 days of continuous hypoxia, the mean right ventricular systolic pressure in the hypoxia model control group was (25.55±2.29) mmHg, which was significantly higher than that in the normoxia control group (17.54±1.48) mmHg, with a statistically significant difference (P<0.001).

After the CBD treatment, the mean right ventricular systolic pressure in the 10 mg/kg experimental group was (16.90±2.31) mmHg, which was significantly lower than that in the hypoxia model control group, with a statistically significant difference (P<0.001); the mean right ventricular systolic pressure in the 50 mg/kg experimental group was (17.92±2.37) mmHg, which was also significantly lower than that in the model group, but there was no significant difference in the results of the two dose treatment groups (10 mg/kg and 50 mg/kg).

Figure 2:
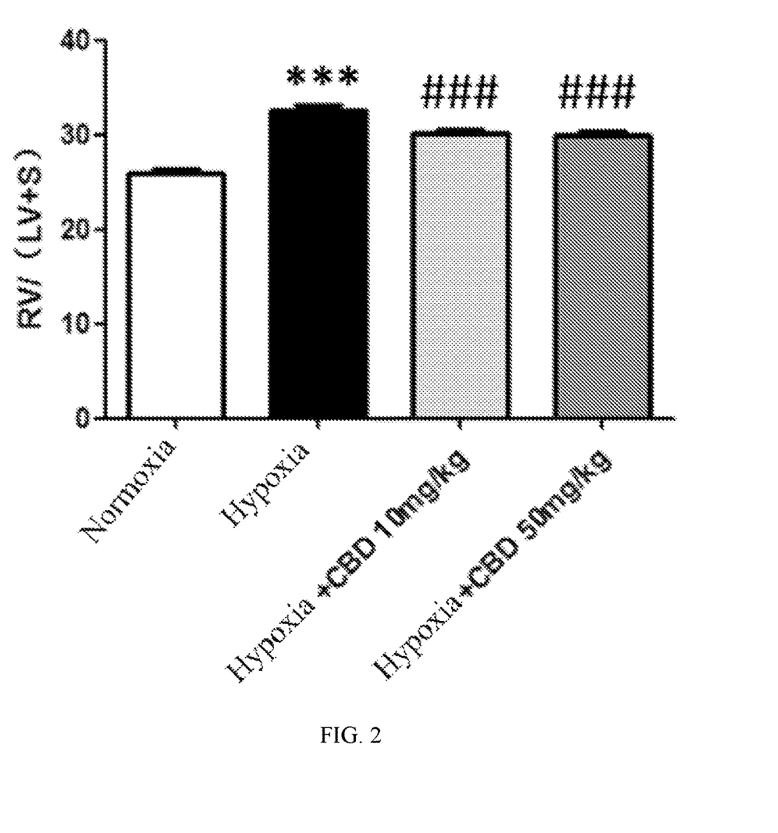
FIG. 2: CBD reduces right ventricular hypertrophy caused by hypoxia, N=10/the numeral value is the average value±standard error, and when the wild-type normoxia group is taken as a reference, ***$P<0.001$; and when the wild-type hypoxia group is taken as a reference, ####$P<0.001$.
Figure 3A:
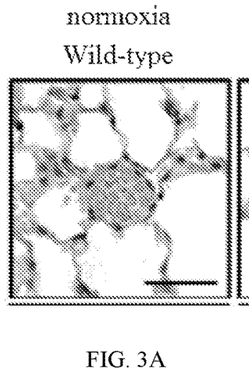
FIG. 3A shows results of pulmonary arteriolar vascular HE staining, wherein the sample is a paraffin section of lung tissue of mice from group 1.
Figure 3B:
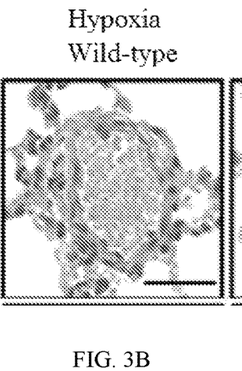
FIG. 3B shows results of pulmonary arteriolar vascular HE staining, wherein the sample is a paraffin section of lung tissue of mice from group 2.
Figures 3C, 3D:
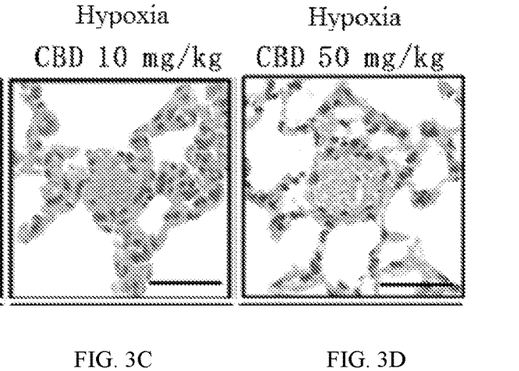
FIG. 3C shows results of pulmonary arteriolar vascular HE staining, wherein the sample is a paraffin section of lung tissue of mice from group 3.
FIG. 3D shows results of pulmonary arteriolar vascular HE staining, wherein the sample is a paraffin section of lung tissue of mice from group 4.
Figure 3E:
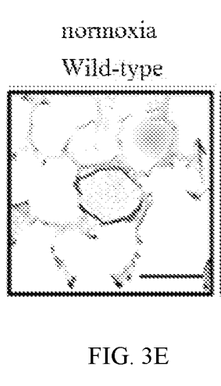
FIG. 3E shows results of elastic fiber staining, wherein the sample is a paraffin section of lung tissue of mice from group 1.
Figure 3F:
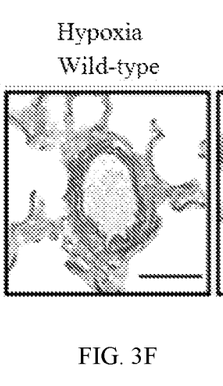
FIG. 3F shows results of elastic fiber staining, wherein the sample is a paraffin section of lung tissue of mice from group 2.
Figure 3G:
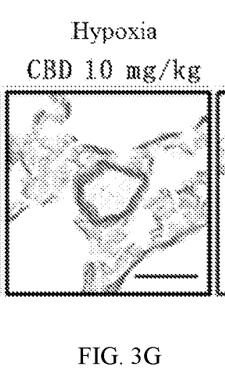
FIG. 3G shows results of elastic fiber staining, wherein the sample is a paraffin section of lung tissue of mice from group 3.
Figure 3H:
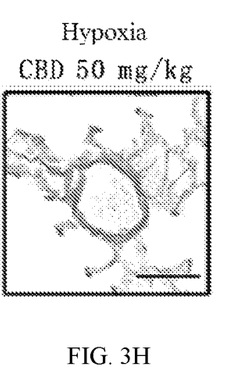
FIG. 3H shows results of elastic fiber staining, wherein the sample is a paraffin section of lung tissue of mice from group 4.
Figure 4:
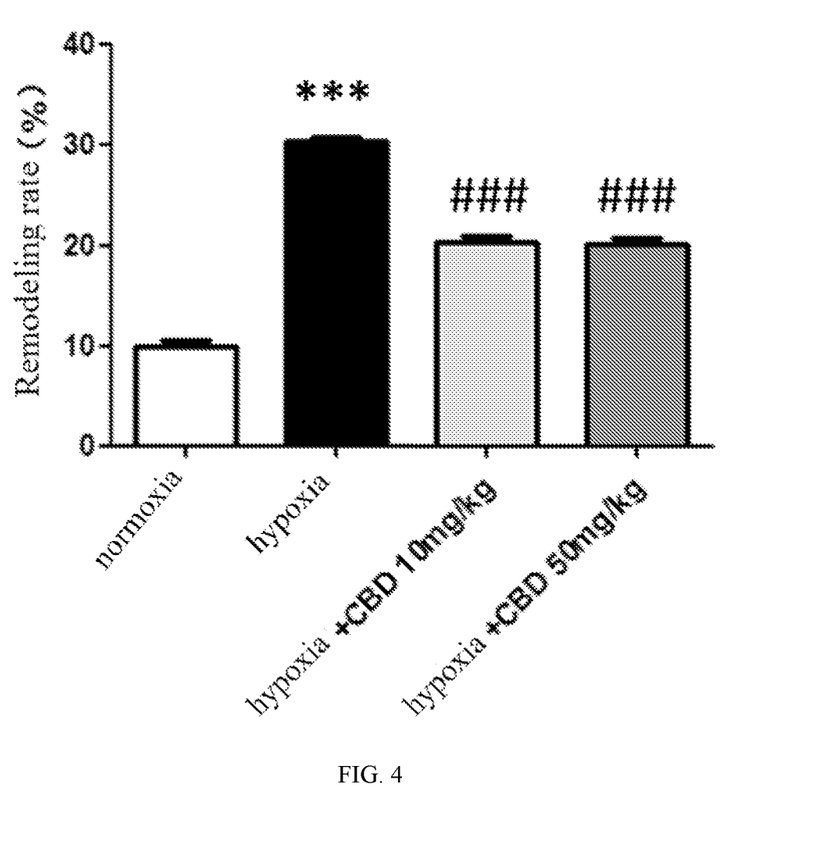
FIG. 4: CBD reduces the vascular remodeling rate caused by hypoxia, N=the numeral value is the average value±standard error, and when the wild-type normoxia group is taken as a reference, ***$P<0.001$; and when the wild-type hypoxia group is taken as a reference, ####$P<0.01$.

(2) The CBD Treatment Significantly Inhibited the Right Ventricular Hypertrophy Index of the PAH Mice The results were as shown in FIG. 2.

The right ventricular hypertrophy index of the mice in the model group was (32.62±1.41)%, which was significantly higher than that of the mice in the normoxia control group (25.99±1.17)%. After the CBD treatment, the right heart index of the mice in the 10 mg/kg and 50 mg/kg experimental groups were (30.18±1.01)% and (29.90±1.19)%, respectively, which were significantly lower than that of the model group, with a statistically significant difference (p<0.001), but there was no significant difference between the different dose treatment groups.

(3) Pathological Changes of Pulmonary Arterioles

The results were as shown in FIGS. 3A-3H and 4.

In the hypoxia model group, the vascular wall of the mice was significantly thickened and remodeled. After the CBD treatment, the pulmonary arteriole remodeling was significantly reduced, and the remodeling rate was significantly reduced.

Both dose groups of cannabidiol could reduce the right ventricular systolic pressure and inhibit the right ventricular (RV) hypertrophy index; and the pathological remodeling had an improvement effect, including the reduction of arterial medial wall thickness ratio, the reduction of vascular wall medial cross-sectional area ratio and the reduction of the right ventricular hypertrophy.

Example 2: In Vitro Experiment of Treating LPS-Induced Macrophages with Cannabidiol 1. Experimental Animals, Reagents and Instruments
2-month-old C57BL/6 mice (Laboratory Animal Center of Academy of Military Medical Sciences, SPF grade)
RPMI-1640 (Sigma)
Cannabidiol (CBD, Yunnan Hansu Biotechnology Co., Ltd)
LPS (Sigma)
Fluorescence quantitative PCR instrument (Roche)

2. Experimental Method

Primary alveolar macrophages were isolated according to the method by Yang et al. (Yang, H. M., Ma, J. Y., Castranova, V., and Ma, J. K. (1997). Effects of diesel exhaust particles on the release of interleukin-1 and tumor necrosis factor-alpha from rat alveolar macrophages. Experimental lung research 23, 269-284): two-month-old mice were taken and injected intraperitoneally with pentobarbital to be anesthetized. The mice were fixed at a supine position, and disinfected at the neck, and the neck skin was cut open to strip gland muscles and expose the trachea. A small opening was cut in an upper part of the trachea without cutting off. A small white pipette tip was inserted onto a 1 ml pipette to pipette 1 ml PBS at 4° C. (free of $Ca^{2+}$, free of $Mg^{2+}$, 0.6 mm EDTA) [50 ml PBS+0.00876 g EDTA] into the lung from the opening, and then pipetted out from the opening after blowing in. Then fresh PBS was taken and pipetted into and out from the opening repeatedly for 3-4 times. The collected alveolar irrigation solution was centrifuged at 200×g for 5 minutes, and the supernatant was discarded. The cells were washed once with a serum-free RPMI-1640 culture medium and centrifuged at 200×g for 5 minutes. The cells were resuspended by adding a serum-containing RPMI-1640 and then inoculated. The cells were subjected to adherence for 2 h, and then washed for three times with PBS. A serum-containing RPMI-1640 was added, and the cells were cultured under 5% carbon dioxide at 37° C.

Alveolar macrophages of the mice were taken and randomly divided into six treatment groups (about $5\times10^6$ cells in each group), wherein the first group was a negative control; the second group was induced by 100 ng/mL LPS (LPS was added into the culture medium) to simulate a inflammatory reaction model in vivo; the third group was a CBD control group (5 μM CBD was added into the culture medium); and the fourth group was pre-treated with 0.5 μM CBD for 0.5 h, and then induced by 100 ng/mL LPS (0.5 μM CBD and 100 ng/mL LPS were added into the culture medium). The fifth group was pre-treated with 1 μM CBD for 0.5 h and then induced by 100 ng/mL LPS (1 μM CBD and 100 ng/mL LPS were added into the culture medium). The sixth group was pre-treated with 5 μM CBD for 0.5 h and then induced by 100 ng/mL LPS (5 μM CBD and 100 ng/mL LPS were added into the culture medium). The cells were collected after treatment for 5 h, and the expression changes of cellular inflammation cytokines TNF-α, IL-6 and $MgI_2$ in each group were detected by the fluorescence quantitative PCR instrument.

```
Primers for detecting TNF-α:
forward primer:
                                            (SEQ ID NO: 1)
CCCTCACACTCAGATCATCTTCT reverse primer:
                                            (SEQ ID NO: 2)
GCTACGACGTGGGCTACAG Primers for detecting IL-6:
forward primer:
                                            (SEQ ID NO: 3)
GAGGATACCACTCCCAACAGACC reverse primer:
                                            (SEQ ID NO: 4)
AAGTGCATCGTTGTTCATACA Primers for detecting MgI₂:
forward primer:
                                            (SEQ ID NO: 5)
AGGCAGCTGCTATTGGTTCTCTGA reverse primer:
                                            (SEQ ID NO: 6)
AGTTGACCACCACCAGGTGAGAAT
```

3. Experimental Results

Figure 5:
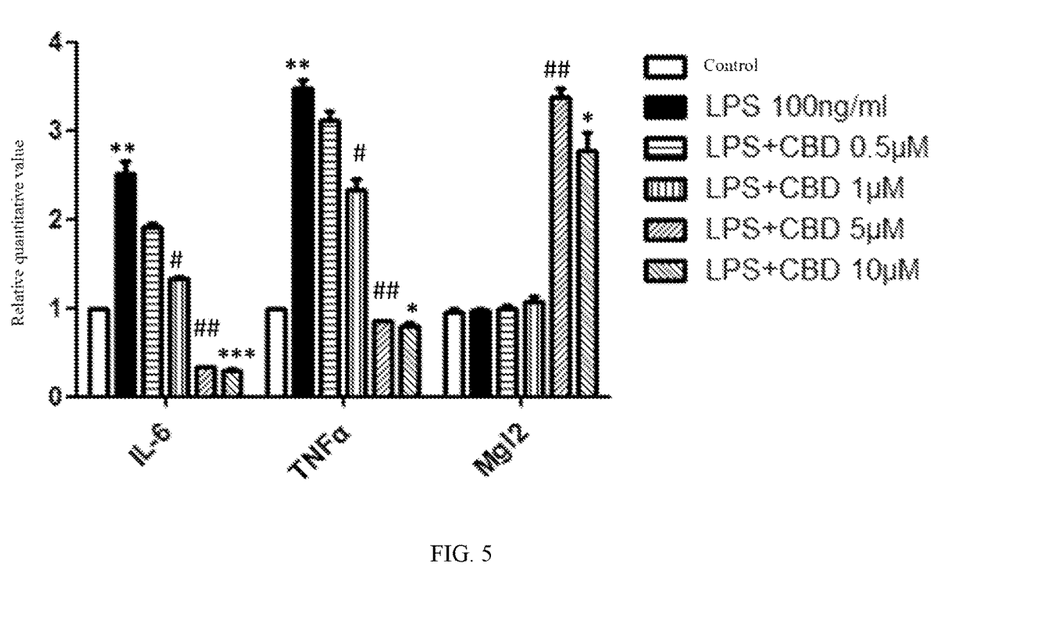
FIG. 5: CBD inhibits LPS-induced activation of primary alveolar macrophages in vitro, The numerical value is the average value±standard error, and when the negative control group is taken as a reference, *$P<0.05$, **$P<0.01$; and when the LPS treatment group is taken as a reference, #$P<0.05$, ##$P<0.01$.

The results were as shown in FIG. 5.

The results showed that CBD could significantly inhibit the expression of LPS-induced inflammation-related TNF-α and IL-6 in a dose-dependent manner, and promote the expression of $MgI_2$, a gene that inhibited inflammation.

Although specific embodiments of the present invention have been described in detail, those skilled in the art will understand the following things. In light of all the teachings that have been disclosed, various modifications and replacements can be made to those details, which are all within the protection scope of the present invention. The full scope of the present invention is given by the appended claims and any equivalents thereof.

---

The invention claimed is:

1. A method of treating pulmonary arterial hypertension in a human in need thereof consisting essentially of administering to the human in need thereof 0.1 mg/kg body weight –100 mg/kg body weight of isolated cannabidiol to effectively treat the pulmonary arterial hypertension in the human in need thereof.

2. The method of claim 1, wherein the pulmonary arterial hypertension is primary or secondary.

3. The method of claim 1, wherein the administering is performed orally.

* * * * *